United States Patent
Guo et al.

(10) Patent No.: US 12,419,311 B2
(45) Date of Patent: Sep. 23, 2025

(54) SPINOSAD HIGH-YIELD STRAIN AND USE THEREOF

(71) Applicants: Shandong Lukang Pharmaceutical Co., Ltd., Shandong (CN); Shandong Lukang Biological Pesticide Co., Ltd., Shandong (CN)

(72) Inventors: Qiang Guo, Shandong (CN); Haifeng Cao, Shandong (CN); Zhigang Jin, Shandong (CN)

(73) Assignees: Shandong Lukang Pharmaceutical Co., Ltd, Shandong (CN); Shandong Lukang Biological Pesticide Co., Ltd, Shandong (CN)

( * ) Notice: Subject to any disclaimer, the term of this patent is extended or adjusted under 35 U.S.C. 154(b) by 0 days.

(21) Appl. No.: 18/722,480

(22) PCT Filed: Dec. 20, 2022

(86) PCT No.: PCT/CN2022/140418
§ 371 (c)(1),
(2) Date: Jun. 20, 2024

(87) PCT Pub. No.: WO2023/116710
PCT Pub. Date: Jun. 29, 2023

(65) Prior Publication Data
US 2024/0423212 A1    Dec. 26, 2024

(30) Foreign Application Priority Data
Dec. 21, 2021  (CN) .................. 202111574398.6

(51) Int. Cl.
*A01N 63/20*   (2020.01)
*A01P 5/00*    (2006.01)
*A01P 7/02*    (2006.01)
*A01P 7/04*    (2006.01)
*A61K 35/74*   (2015.01)
*C12N 1/20*    (2006.01)
*C12R 1/01*    (2006.01)

(52) U.S. Cl.
CPC ............. *A01N 63/20* (2020.01); *A01P 5/00* (2021.08); *A01P 7/02* (2021.08); *A01P 7/04* (2021.08); *A61K 35/74* (2013.01); *C12N 1/205* (2021.05); *C12R 2001/01* (2021.05)

(58) Field of Classification Search
CPC . A01N 63/20; C12N 1/205; A01P 7/04; A01P 5/00; A61K 35/74; C12R 2001/01
See application file for complete search history.

(56) References Cited

FOREIGN PATENT DOCUMENTS

| | | |
|---|---|---|
| CN | 101928670 A | 12/2010 |
| CN | 102533551 A | 7/2012 |
| CN | 102676393 A | 9/2012 |
| CN | 104974974 A | 10/2015 |
| CN | 113444659 A | 9/2021 |

OTHER PUBLICATIONS

Written Opinion (including translation) for PCT/CN2022/140418, mailed Mar. 12, 2023, pp. 1-6.
International Search Report for International Patent Application No. PCT/CN2022/140418 mailed on Mar. 12, 2023, 6 pages.

*Primary Examiner* — Louise W Humphrey
*Assistant Examiner* — Rachel Emily Martin
(74) *Attorney, Agent, or Firm* — Bayramoglu Law Offices LLC

(57) ABSTRACT

Provided are a spinosad high-yield strain and the use thereof. The strain has a deposit number of CCTCC NO: M20211261, and the strain can produce various types of spinosad with high yields.

27 Claims, 3 Drawing Sheets
Specification includes a Sequence Listing.

| Name | Molecular Formula | Molecular Weight | Structural Formula |
|---|---|---|---|
| Spinosad A iso | C41H65NO10 | 731.95 |  |
| Spinosad B | C40H63NO10 | 717.93 |  |
| Spinosad E | C40H63NO10 | 717.93 |  |
| Spinosad H | C40H63NO10 | 717.93 |  |
| Spinosad J | C40H63NO10 | 717.93 |  |
| Spinosad K | C40H63NO10 | 717.93 |  |
| Spinosad L | C41H65NO10 | 731.95 |  |
| Spinosad L2 | C41H65NO10 | 731.95 |  |
| Spinosad L3 | C41H65NO10 | 731.95 |  |
| Spinosad P | C39H61NO10 | 703.90 |  |
| Spinosad P-CH2 | C38H59NO10 | 689.87 |  |

SEQUENCE LISTING

```
Sequence total quantity: 1
SEQ ID NO: 1            moltype = DNA  length = 1518
FEATURE                 Location/Qualifiers
source                  1..1518
                        mol_type = genomic DNA
                        organism = Saccharopolyspora spinosa
SEQUENCE: 1
aaaggaggtg atccagccgc accttccggt acggctacct tgttacgact tcgtcccaat   60
cgccagtccc accttcgacc actccccca caagggttgg gccatgggct tcgggtgtta  120
ccgactttca tgacgtgacg ggcggtgtgt acaaggcccg ggaacgtatt caccgcagca  180
atgctgatct gcgattacta gcgactccga cttcacgagg tcgagttgca gacccgatc   240
cgaactgaga ccggctttaa gggattcgct ccacctcacg atatcgccac cctctgtacc  300
agccattgta gcatgtgtga agccctgggc ataaggggca tgatgacttg acgtcatccc  360
caccttcctc cgagttgacc ccggcagtcc cccacgagtc cccggcataa cccgctggca  420
acatagggca agggttgcgc tcgttgcggg acttaaccca acatctcacg acacgagctg  480
acgacagcca tgcaccacct gtacaccaac cacaagggaa accccatctc tggagctgtc  540
tagtgcatgt caaacccagg taaggttctt cgcgttgcat cgaattaatc cacatgctcc  600
gccgcttgtg cgggccccgt caattccttt gagttttagc cttgcggccg tactcccag   660
gcggggcgct taatgcgtta gctacggcac ggaaacagtg gaacccatcc ccacacctag  720
cgcccaacgt ttacggcgtg gactaccagg gtatctaatc ctgttcgctc cccacgcttt  780
cgctcctcag cgtcagtatc ggcccagaga cccgccttcg ccaccggtgt tcctcctgat  840
atctgcgcat ttcaccgcta caccaggaat tccagtctcc cctaccgaac tcaagtctgc  900
ccgtatcgac cgcaagccca cagttaagct gcaggttttc acggccgacg cgacaaaccg  960
cctacgagct ctttacgccc aataaatccg gacaacgctc gcaccctacg tattaccgcg 1020
gctgctggca cgtagttagc cggtgcttct tctacaccta ccgtcacccg aaggcttcgt 1080
cgatgtcgaa agaggtttac aacccgaagg ccgtcatccc ccacgcggcg ttgctgcgtc 1140
aggctttcgc ccattgcgca agattcccca ctgctgcctc ccgtaggagt ctgggccgtg 1200
tctcagtccc agtgtggccg gtcaccctct caggccggct accgctcgtc gccttggtag 1260
gccatcaccc caccaacaag ctgataggcc gcggactcat cctgcaccgc cagaactttc 1320
cacacaccac catgcgataa tgtgtcatat ccggtattag accccgtttc caaggcttat 1380
cccagagtgc agggcagatt acccacgtgt tactcacccg ttcgccactc atccacaccc 1440
gaaagatgctt cagcgttcga cttgcatgtg ttaagcacgc cgccagcgtt cgtcctgagc 1500
caggatcaaa ctctccaa                                                1518
```

SPINOSAD HIGH-YIELD STRAIN AND USE THEREOF

CROSS REFERENCE TO RELATED APPLICATIONS

This application is a U.S. national stage application under 35 U.S.C. § 371 of International Application No. PCT/CN2022/140418, filed internationally on Dec. 20, 2022, which claims the benefit and priority of Chinese Application No. 202111574398.6 filed Dec. 21, 2021, the disclosure of which are hereby incorporated by reference in its entirety.

FIELD OF THE INVENTION

The present disclosure belongs to the field of biological fermentation technology. Particularly, the present disclosure relates to a spinosad high-yield strain and use thereof.

BACKGROUND OF THE INVENTION

As an indispensable means of production in agricultural production, pesticides have made great contributions to agricultural development and human food supply. Pesticides mainly include three categories: germicides, insecticides and herbicides. There are thousands of formulated pesticide products worldwide that contain chemicals as active ingredients. The above pesticide product includes antibacterial agents, acaricides, germicides, nematicides, animal medicinal bath agents, pest bird-killing agents and disinfectants. Chemical control has the advantages of rapid effectiveness, significant effects, ease of use, no regional or seasonal restrictions, etc. Its usage for large-scale control is still the main means of pest control.

However, the long-term and extensive use of chemical pesticides has led to a series of serious problems while controlling pests for the benefit of humans, including widespread insect resistance, the emergence of secondary pests, hazards to human and animal health and harmful effects on fish and birds, environmental pollution and increased economic costs of new pesticides.

For the human body, pesticides often cause damage via the skin, respiratory system and digestive system, which may cause acute toxic reactions to pesticides such as poisoning, and skin and eye irritation, as well as possible long-term effects, such as causing genetic mutations in cells in the body, changing genetic cell mechanisms, leading to cancer or teratogenesis.

According to the pesticide toxicity classification standard of China, spinosad belongs to low-toxic pesticides. Spinosad belongs to broad-spectrum pesticides that may effectively control pests of the Lepidoptera, Diptera and Thysanoptera, and may effectively prevent and control certain pest species in Coleoptera and Orthoptera that devour leaves in large quantities. It is relatively low toxic to mammals and birds and only has mildly moderate toxicity to aquatic animals. Taking all of the above factors into consideration, spinosad is usually the first choice when conducting integrated pest management.

At present, spinosad is still produced by *Saccharopolyspora spinosa* through aerobic fermentation. Although there are several patents report on increasing the production of spinosad by improving the culture medium or the control method of the fermentation tank, it is difficult to achieve scale production through fermentation optimization because the fermentation yield of the strain itself is poor.

Therefore, it is urgent to find new strains with high spinosad yield to solve the problem of low spinosad production.

SUMMARY OF THE INVENTION

In order to overcome the deficiencies in the prior art, the purpose of the present disclosure is to provide a new spinosad high-yield strain, which may produce multiple spinosads with high yield, wherein the total shake flask yield of spinosad A and spinosad D is about 6 g/L.

In one aspect, the present disclosure provides a spinosad high-yield strain, which is a soil actinomycete of the genus *Saccharopolyspora*, namely *Saccharopolyspora spinosa* W618, the deposit accession number thereof is CCTCC NO: M 20211261.

In another aspect, the present disclosure provides a pesticidal composition, the composition comprises the strain.

In some embodiments, the composition further comprises one or more selected from the following compounds: organophosphorus compounds, carbamate compounds, synthetic pyrethroid compounds, acyl urea compounds, other types of insect growth regulators and insect hormone analogs, neonicotinoids and other nicotinoid compounds, macrolide compounds, other insecticidal, acaricidal, molluscicidal and nematicidal compounds or active ingredients, and phagocytic stimulants.

In some embodiments, the pesticidal composition may further comprise a pharmaceutically acceptable carrier, e.g. a liquid carrier, or a solid carrier.

In some embodiments, the liquid carrier may be selected from one or more of aliphatic ketones (e.g. cyclohexanone) and complex alcohols (e.g. 2-ethoxyethanol) and aromatic compounds, especially xylene and petroleum fractions, especially the high-boiling naphthalene and olefin parts of petroleum e.g. heavy aromatic petroleum naphtha.

In some embodiments, the solid carrier may be selected from one or more of attapulgite clay, montmorillonite clay, diatomaceous earth or purified silicate.

In some embodiments, the dosage form of the pesticide composition can be selected from wettable powders, soluble powders, emulsifiable concentrates, aqueous suspensions, dispersible oil suspensions, aqueous emulsions, aerosols, microemulsions and water-dispersible granules.

In another aspect, the present disclosure provides a method for preparing the aforementioned pesticidal composition, the method comprises seeding the aforementioned strain into a culture medium for fermentation culturing to prepare the pesticidal composition.

In some embodiments, the medium comprises seed culture medium and fermentation culture medium.

In some embodiments, the pH of the seed culture medium and/or fermentation culture medium is adjusted with a pH adjusting agent; preferably, the pH adjusting agent is a base; more preferably, the base is one or more of sodium hydroxide, potassium hydroxide, sodium carbonate, sodium bicarbonate.

In some embodiments, the fermentation condition is 200-300 rpm, 10-40° C., and 50-70% humidity.

In some embodiments, the fermentation condition is 250 rpm, 28° C., and 60% humidity.

In another aspect, the present disclosure provides the use of the aforementioned pesticidal composition in the manufacture of a medicament for killing insects, killing animals of subclass Acari, killing nematodes.

In some embodiments, the medicament for killing insects, killing animals of subclass Acari, killing nematodes can be applied to an animal associated with agriculture, e.g. cattle, pig, sheep, goat, horse or donkey, or a plant, e.g. soybean, corn, sugarcane, rape, potato, cotton, rice, coffee, citrus, almond, tea.

In some embodiments, the medicament may be a medicament for enterally administering to an animal, e.g. a medicament in the form of a tablet, a capsule, a drink, a drench, a granule, a paste, a bolus, a suppository.

In some embodiments, the medicament may be a medicament for parenterally administering to an animal, e.g., a medicament in the form for administering by means of injection (including intramuscular, subcutaneous, intravenous, intraperitoneal, etc.), implantation, showering, dipping, spraying, pouring, dripping, washing, dusting.

In some embodiments, the medicament may be a medicament in the form for administering to a plant by means of spraying, pouring, dripping, washing, dusting.

*Saccharopolyspora spinosa* W618 was deposited in China Center for Type Culture Collection (CCTCC, address: Wuhan University, Wuhan, China) on Oct. 27, 2021, with the deposit accession number CCTCC NO: M 20211261.

The pesticide composition containing *Saccharopolyspora spinosa* W618 and/or its fermentation product and/or its bacterial suspension and/or its culture broth may effectively control pests of Lepidoptera, Diptera and Thysanoptera, and may effectively prevent and control certain pest species in Coleoptera and Orthoptera that devour leaves in large quantities.

Additional aspects and advantages of the present disclosure will be given in part in the following description, and will be apparent in part from the following description, or be learned through the practice of the present disclosure.

DETAILED DESCRIPTION OF THE EMBODIMENTS

Definitions

Figure 1:
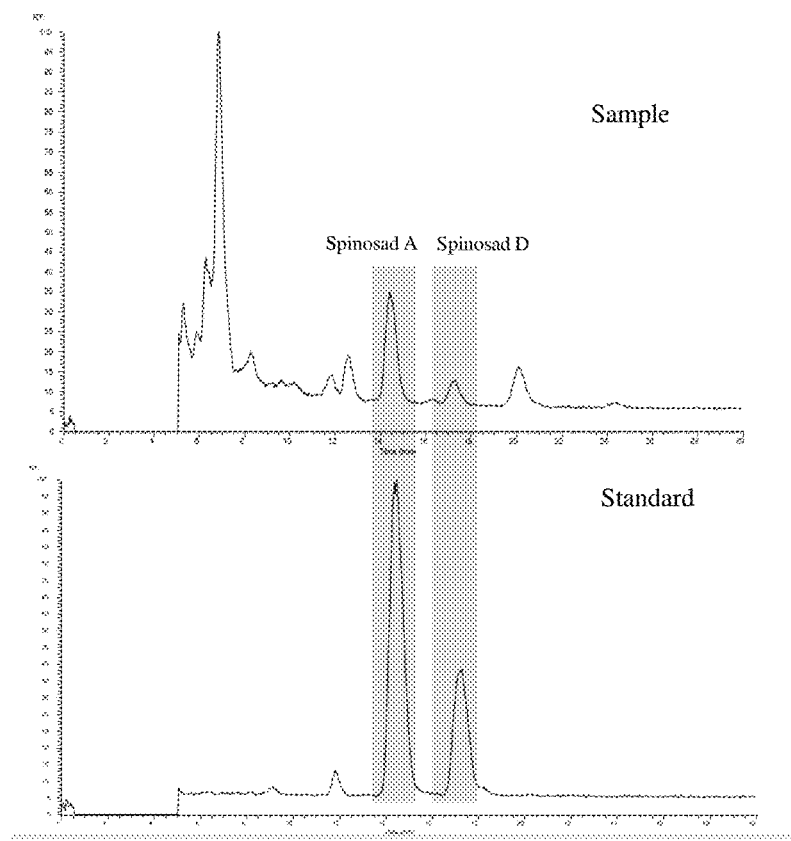
FIG. 1 shows the results of detecting the components of the fermentation product using LC-MS, wherein the upper figure is the result of detecting the fermentation product in Example 1, and the lower figure is the result of detecting the spinosad standard substance.
Figure 2:
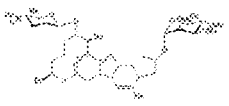
FIG. 2 shows the results of detecting various spinosads in the fermentation product using LC. Spinosad A-iso, spinosad B, spinosad E, spinosad H, spinosad J, spinosad K, spinosad L, spinosad L2, spinosad L3, spinosad P, and spinosad P-CH2 may also be detected in the fermentation product, in addition to spinosad A and spinosad D.
Figure 2:
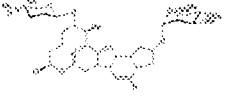
Figure 2:
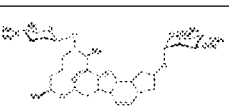
Figure 2:
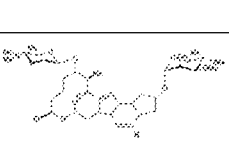
Figure 2:
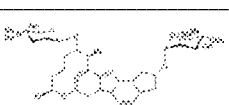
Figure 2:
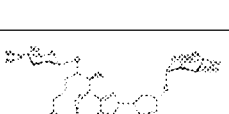
Figure 2:
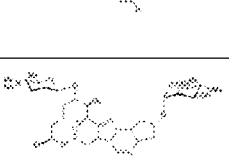
Figure 2:
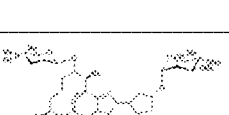
Figure 2:
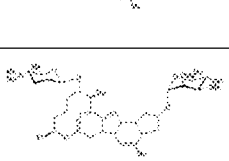
Figure 2:
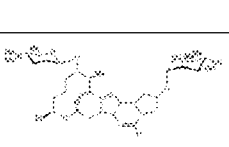
Figure 2:
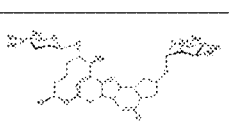
Figure 3:
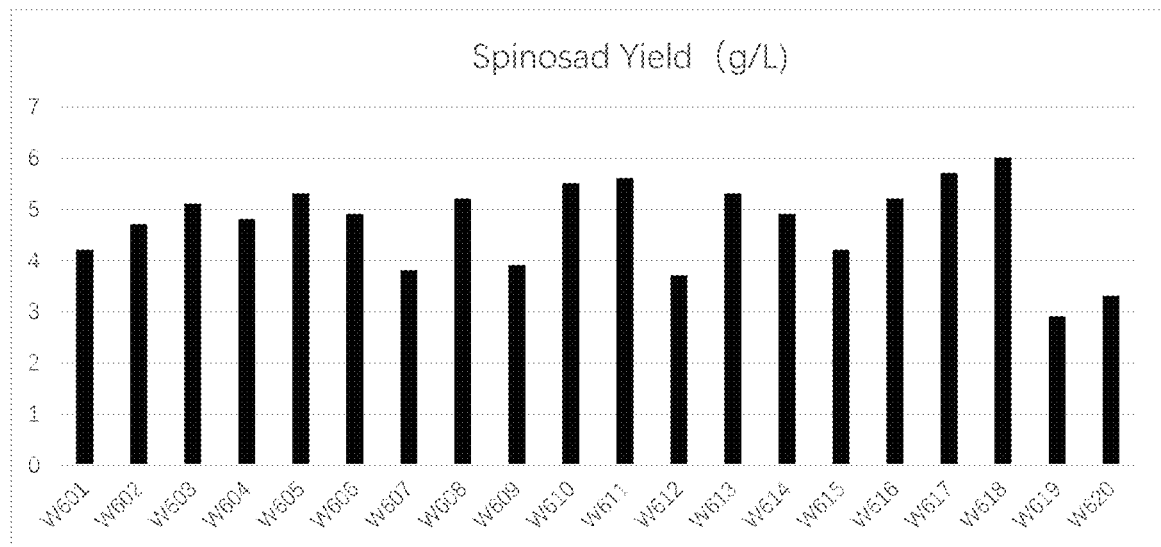
FIG. 3 shows the yield results of 20 strains of *Saccharopolyspora spinosa* strain W600 screened after 6 rounds of mutagenesis and fermented one by one, among which the *Saccharopolyspora spinosa* strain with the highest yield is W618.
Figure 4:
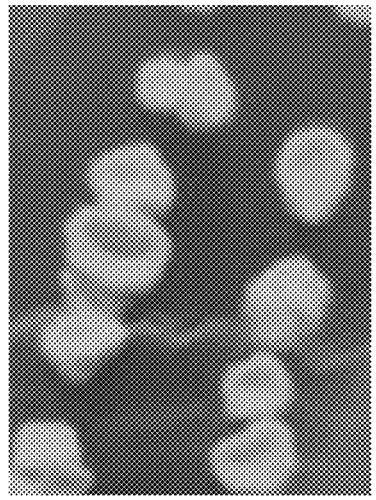
FIG. 4 shows a photograph of mature colonies of the *Saccharopolyspora spinosa* strain W600 seed culture.

The term "fermentation product" as used in the present disclosure refers to the product produced by a method that includes a fermentation step performed using a fermenting organism.

The term "bacterial suspension" as used in the present disclosure refers to a mixture obtained by collecting the fermentation broth through solid-liquid separation by biological separation and extraction technology after the fermentation of the fermentation organism is completed. The separation and collection are usually performed by centrifugation or membrane filtration.

The term "culture broth" as used in the present disclosure refers to a liquid culture containing both a fermenting organism and a culture medium.

The term "plant" as used in the present disclosure includes seedlings, shrubs, and trees. Plants are to be understood as also including those crops which have been rendered tolerant to herbicides or classes of herbicides (e.g. ALS-, GS-, EPSPS-, PP0- and HPPD-inhibitors) by conventional methods of breeding or by genetic engineering. Plants are also to be understood as being those which are obtained by conventional methods of breeding or genetic engineering and which contain so-called output traits (e.g. improved storage capacity, higher nutritional value and improved aroma).

The term "pesticidal composition" as used in the present disclosure refers to a composition having pesticidal effect against pests.

As used with respect to the veterinary field, the term "control" means that the pesticidal composition is effective to reduce the incidence of a corresponding parasite in an animal infected with such a parasite to harmless levels. More specifically, as used herein, "control" means that the active compounds are effective in killing the corresponding parasite, inhibiting its growth, or inhibiting its reproduction. In general, when used for animal treatment, these pesticidal compositions according to the present invention can be applied directly. Preferably, these pesticidal compositions may comprise pharmaceutically acceptable carriers and/or adjuvants known in the art.

Specific representative arthropod pests that may be controlled by the "pesticide composition" described in the present disclosure include the following: *Amblyomma americanum, Amblyomma maculatum, Argas persicus, Boophilus microplus, Dermacentor anderson, Dermacentor variabilis, Dermanyssus gallinae, Ixodes ricinus, Rhipicephalus sanguineus, Chorioptes* spp., *Demodex bovis, Demodex canis, Knemidokoptes gallinae, Knemidokoptes mutans, Otobius megnini* (ear tick), *Psoroptes equi, Psoroptes ovis, Sarcoptes scabiei, Aedes, Anopheles, Culex, Culiseta, Bovicola bovis* (cattle bitinglouse), *Callitroga homnivorax* (blowfly), *Chrysops* spp. (deer fly), *Cimex lectularius, Ctenocephalides canis, Ctenocephalides felis, Culicoides* spp. (midges, sandflies, punkies, or no-see-ums), *Damaliniaviridis, Cochliomyia* spp., *Dermatobia* spp., *Gastrophilushaemorrhoidalis, Gastrophilus intestinalis, Gastrophilus nasalis, Glossina* spp., *Haematobia irritans, Hypoderma bovis, Hypoderma lineatum, Lucilia* spp., *Melophagus ovinus, Musca* spp., *Oestrus ovis, Phormia regina, Stomoxys calcitrans, Hydrotaeairritans* (head fly), *Linognathus ovillus* (body louse), *Linognathus pedalis* (foot louse), *Linognathusvituli, Haematopus asini, Haematopinus eurysternus, Haematopus ovillus* (bodylouse), *Haematopus suis, Pediculus* spp., *Solenopotes capillatus, Phlebotomus* spp., *Psorophora* spp. (mosquito), *Pthirus* spp. (lice), *Reduvius* spp., *Simulium* spp., *Tabanus* spp., *Tenebrio* spp., *Triatoma* spp. Pesticidal compositions provided by the present disclosure may be used to control internal and external parasites. These pesticidal compositions are applied (e.g. administered) in a known manner (by enteral administration in the form of, for example, tablets, capsules, drinks, drenches, granules, pastes, boluses, suppositories; by parenteral administration to animals or phytotherapy, for example, by means of injection (including intramuscular, subcutaneous, intravenous, intraperitoneal, etc.), implantation, by skin application in the form of, for example, showering or dipping, spraying, pouring and dripping, washing, dusting and with the help of shaped articles containing the pesticidal composition (e.g., roller rings, ear tags, tail tags, limb bands, halters, manufacturing devices and the like)).

The existing method for preparing spinosad compounds using *Saccharopolyspora spinosa* has a low yield of spinosad compounds, resulting in a high cost for industrial preparation of spinosad compounds. The inventor obtained a high-yield strain for spinosad, *Saccharopolyspora spinosa* W618, from a large number of strains through screening of spinosad-producing conditions and multiple rounds of ultraviolet mutagenesis. Spinosad was produced by fermentation using the strain with a shake flask yield of up to 6 g/L. Therefore, *Saccharopolyspora spinosa* W618 may be developed as an industrial strain with high production of spinosad.

In one aspect, the present disclosure provides a spinosad high-yield strain, which is a soil actinomycete of the genus *Saccharopolyspora*, namely *Saccharopolyspora spinosa* W618, the deposit accession number thereof is CCTCC NO: M 20211261.

In another aspect, the present disclosure provides a pesticidal composition, the composition comprises the *Saccharopolyspora spinosa* mentioned above.

In some embodiments, the pesticidal composition comprises one or more of more than 30 structurally similar components such as spinosad A, spinosad A-iso, spinosad B, spinosad C, spinosad D, spinosad E, spinosad F, spinosad G, spinosad H, spinosad J, spinosad K, spinosad L, spinosad L2, spinosad L3, spinosad P, and spinosad P-$CH_2$.

In some preferred embodiments, the pesticidal composition comprises spinosad A and spinosad D.

In some embodiment, the composition further comprises one or more selected from the following compounds: organophosphorus compounds, carbamate compounds, synthetic pyrethroid compounds, acyl urea compounds, other types of insect growth regulators and insect hormone analogs, neonicotinoids and other nicotinoid compounds, macrolide compounds, other insecticidal, acaricidal, molluscicidal and nematicidal compounds or active ingredients, and phagocytic stimulants.

In some preferred embodiments, the organophosphorus compounds are selected from one or more of the following compounds: acephate, azinphos-methyl, cadusafos, trichloronate, chlorpyrifos, coumaphos. dematon, demeton, diazinon, dichlorvos, dimethoate, EPN, erthoate, ethoprophos, etrimfos, fenamiphos, fenitrothion, fensulfothion, fenthion, fonofos, formothion, fosthiazate, heptenophos, malathion, methamidophos, methyl parathion (methyl 1605), mevinphos, monocrotophos, parathion (1605), phorate, phosalone, phosmet, phosphamidon, phosphocarb, phoxim, profenofos, propaphos, propetamphos, prothiofos, pirimiphos-methyl, pirimiphos-ethyl, quinalphos, sulprofos, tebupirimphos, temephos, terbufos, tetrachlorvinphos, thiafenox, thiometon, triazophos and trichlorfon.

In some preferred embodiments, the carbamate compounds are selected from one or more of the following compounds: aldicarb, bendiocarb, benfuracarb, bensultap, BPMC, butoxycarbocim, carbaryl (sevin), furadan (carbofuran), carbosulfan, cloethocarb, ethiofencarb, fenobucarb, furathiocarb, methiocarb, isoprocarb, methomyl, methomyl, pirimicarb, promecarb, propoxur, thiodicarb and thiofurox.

In some preferred embodiments, the synthetic pyrethroid compounds are selected from one or more of the following compounds: acrinathrin, allethrin, β-cyfluthrin, bifenthrin, bioresmethrin, cyfluthrin, cyhalothrin, λ-cyhalothrin, γ-cyhalothrin, cypermethrin, α-cypermethrin, ζ-cypermethrin, deltamethrin, esfenvalerate, fenvalerate, fenfluthrin, fenpropathrin, flucythrinate, flumethrin, fluvalinate, τ-fluvalinate, fubfenprox, permethrin, protrifenbute, resmethrin, silafluofen, tefluthrin, tetramethrin, tralomethrin, pyrethroids safe for fish, e.g. etofenprox, natural pyrethroids, tetramethrin, S-allethrin, fenfluthrin and prallethrin.

In some preferred embodiments, the acyl urea compounds, other types of insect growth regulators and insect hormone analogs are selected from one or more of the following compounds: buprofezin, chromfenozide, chlorfluazuron, diflubenzuron, fenoxycarb, flufenoxuron, halofenozide, hexaflumuron, hydroprene, lufenuron, methoprene, methoxyfenozide, novaluron, pyriproxyfen, teflubenzuron and benzamide, N-[3,5-dichloro-2-fluoro-4-(1,1,2,3,3,3-hexafluoropropoxy)phenyl]-N'-(2,6-difluorobenzoyl)urea.

In some preferred embodiments, the neonicotinoids and other nicotinoid compounds are selected from one or more of the following compounds: acetamiprid, AKD-1022, cartap, TI-435, clothiamidin, MTI-446, dinotefuran, imidacloprid, nicotine, nitenpyram, thiamethoxam, thiacloprid.

In some preferred embodiments, the macrolide compounds are selected from one or more of the following compounds: avermectin, milbemycin, abamectin, ivermectin, milbemycin and emamectin benzoate.

In some preferred embodiments, the other insecticidal, acaricidal, molluscicidal and nematicidal compounds or active ingredients are selected from one or more of the following compounds: allethrin, amitraz, azdirachtin, azocyclotin, bifenazate, bromopropylate, chlordimeform, chlorfenapyr, chlofentezine, chlorobenzilate, chlordane, cyhexatin, cyromazine, DDT, dicofol, dieldrin, DNOC, endosulfan, ethoxazole, fenazaquin, cyhexatin, fenpyroximate, β-fenpyroximate, fipronil, fluoropheniminothiazole hexythiazox, IKI-220, indoxacarb, lindane, methiocarb, metaldehyde, methoxychlor, neem, petroleum and vegetable oils, pyridaben, pymetrozine, pyrimidifen, rotenone, S-1812, S-9539, spirodiclofen, sulphur, tebufenpyrad, tetradifon, menazon, insect-active plant extracts, preparations containing insect-active nematodes, preparations obtainable from *Bacillus subtilis, Bacillus thuringiensis*, nuclear polyhedrosis virus or other genetically modified or naturally occurring organisms, and synergists e.g. piperonyl butoxide, sesamax, safroxan and dodecyl imidazole.

In some preferred embodiments, the phagocytic stimulants are selected from one or more of the following compounds: cucurbitacin, sugar and Coax.

In some embodiments, the pesticidal composition may further comprise a pharmaceutically acceptable carrier, e.g. a liquid carrier, or a solid carrier.

The liquid carrier may be selected from one or more of aliphatic ketones (e.g. cyclohexanone) and complex alcohols (e.g. 2-ethoxyethanol) and aromatic compounds, especially xylene and petroleum fractions, especially the high-boiling naphthalene and olefin parts of petroleum e.g. heavy aromatic petroleum naphtha.

The solid carrier may be selected from one or more of attapulgite clay, montmorillonite clay, diatomaceous earth or purified silicate.

In some preferred embodiments, the dosage form of the pesticide composition is selected from wettable powders, soluble powders, emulsifiable concentrates, aqueous suspensions, dispersible oil suspensions, aqueous emulsions, aerosols, microemulsions and water-dispersible granules.

The pesticidal compositions described herein may be offered by providing together with a pharmaceutically acceptable carrier, for example, baits, emulsion concentrates, powders, emulsified concentrates, fumigants, gels, granules, microcapsules, seed treatments, suspension concentrates, suspoemulsions, tablets, water-soluble liquids, water-dispersible granules or dry flowable wettable powders and ultra-low volume solutions.

Aqueous suspensions or emulsions of pesticidal compositions may be used frequently. Such water-soluble, water-suspendable, or emulsifiable formulations are solids (usually regarded as wettable powders or water-dispersible granules) or liquids (usually regarded as emulsifiable concentrates, or aqueous suspensions). Wettable powders that may be compacted to form water-dispersible granules comprise an intimate mixture of a pesticidal composition, a carrier and a surfactant. The carrier is typically selected from attapulgite clay, montmorillonite clay, diatomaceous earth or purified silicates. Effective surfactants (from about 0.5% to about 10% of the wettable powder) are selected from sulfonated lignins, fused naphthalene sulfonates, naphthalene sulfonates, alkylbenzene sulfonates, alkyl sulfonates and nonionic surfactants such as ethylene oxide adducts of alkylphenols.

Emulsifiable concentrates of the claimed pesticidal compositions typically range from about 50 to about 500 grams of composition per liter of liquid, equivalent to about 10% to about 50%, dissolved in an inert carrier which is a mixture of a water-immiscible solvent and an emulsifier. Organic solvents include organics, e.g. xylenes, and petroleum fractions, e.g. the high-boiling naphthalene and olefinic fractions of petroleum, including heavy naphtha and aromatic naphtha. Other organics may also be used, such as terpene solvents—rosin derivatives, aliphatic ketones, e.g. cyclohexanone, and complex alcohols. Emulsifiers for emulsifiable concentrates are generally mixed ionic and/or nonionic surfactants such as those mentioned herein or their equivalents.

Aqueous suspensions may be prepared to contain water-insoluble compounds of the pesticidal compositions of the invention, wherein the concentration of these compounds dispersed in an aqueous vehicle generally ranges from about 5 to about 50% by weight. Suspensions are prepared by finely grinding the pesticidal composition and vigorously mixing it in a vehicle of water, surfactants and dispersants. Inert ingredients such as inorganic salts and synthetic or natural gums may also be employed to increase the density and/or viscosity of the aqueous vehicle, as desired.

Precipitating fluids may be prepared by dissolving the active molecule in a water-miscible solvent and a surfactant or surfactant polymer. When the preparations are mixed with water, the active compound precipitates, while the surfactant controls the size of the resulting microcrystalline precipitate. The crystal size may be controlled by selecting a particular mixture of polymer and surfactant.

The pesticidal composition may also be prepared into granules and applied to soil. Pesticidal compositions are dispersed in an inert carrier, usually clay or equivalent. Generally, granules are prepared by dissolving the pesticidal composition in a suitable solvent and coating it on a granular carrier which has been processed to the desired particle size. The particle size is typically between about 0.5 mm and 3 mm. Granules may also be prepared by forming a dough or paste of the carrier and the pesticidal composition, drying the mixture, and pulverizing the dough or paste into the desired particle size.

These pesticidal compositions may also be mixed with suitable organic solvents. Organic solvents are generally mild solvents widely used in agriculture. These combinations are commonly used as sprays. More generally, pesticidal compositions are applied as dispersions in a liquid carrier, wherein the liquid carrier is water. The pesticidal compositions may also be administered as aerosol compositions. The pesticidal composition is dissolved in an inert carrier which is a propellant mixture that generates pressure. Aerosol compositions are packaged in containers wherein the mixture is dispensed through an aerosolizing valve. Propellant mixtures contain low-boiling halogenated hydrocarbons (which may be mixed with organic solvents) or aqueous suspensions pressurized with inert gases or gaseous hydrocarbons.

In another aspect, the present disclosure provides a method for preparing the aforementioned pesticidal composition, the preparation method comprises seeding the strain into a culture medium for fermentation culturing to prepare the pesticidal composition.

In some embodiments, the medium comprises seed culture medium and fermentation culture medium.

In some preferred embodiments, the seed culture medium is composed of: 0.8-1.2 parts by mass of glucose, 0.8-1.2 parts by mass of yeast extract, 0.16-0.24 parts by mass of N-Z amine type A, 1.8-2.4 parts by mass of corn starch, 0.08-0.12 parts by mass of ammonium sulfate, 2-3 parts by mass of cottonseed meal, 0.16-0.24 parts by mass of magnesium sulfate heptahydrate, 80-20 parts by mass of water; preferably, the water is distilled water; more preferably, the seed culture medium is composed of: 1 part by mass of glucose, 1 part by mass of yeast extract, 0.2 parts by mass of N-Z amine type A, 2 parts by mass of corn starch, 0.1 parts by mass of ammonium sulfate, 2.5 parts by mass of cottonseed meal, 0.2 parts by mass of magnesium sulfate heptahydrate, 100 parts by mass of water; preferably, the pH value of the culture medium is 6.8-7.2, preferably 7.0.

In some preferred embodiments, the fermentation medium is composed of: 6.4-9.6 parts by mass of glucose, 0.4-0.6 parts by mass of yeast powder, 0.8-1.2 parts by mass of protein powder, 1.6-2.4 parts by mass of cottonseed meal, 0.32-0.48 parts by mass of trisodium citrate, 0.16-0.24 parts by mass of dipotassium hydrogen phosphate, 0.24-0.36 parts by mass of calcium carbonate, 0.16-0.24 parts by mass of ammonium sulfate, 4-6 parts by mass of rapeseed oil, 80-20 parts by mass of water; preferably, the water is distilled water; more preferably, the fermentation medium is composed of: 8 parts by mass of glucose, 0.5 parts by mass of yeast powder, 1 part by mass of protein powder, 2 parts by mass of cottonseed meal, 0.4 parts by mass of trisodium citrate, 0.2 parts by mass of dipotassium hydrogen phosphate, 0.3 parts by mass of calcium carbonate, 0.2 parts by mass of ammonium sulfate, 5 parts by mass of rapeseed oil, 100 parts by mass of water; preferably, the pH value of the culture medium is 6.8-7.2, preferably 7.0.

In some embodiments, according to the aforementioned preparation method, wherein the fermentation condition is 200-300 rpm, 10-40° C., and 50-70% humidity.

In some preferred embodiments, the fermentation condition is 250 rpm, 28° C., and 60% humidity.

In another aspect, the present disclosure provides a use of the aforementioned pesticidal composition in the manufacture of a medicament for killing insects, killing animals of subclass Acari, killing nematodes.

In some embodiments, the medicament for killing insects, killing animals of subclass Acari, killing nematodes can be applied to an animal associated with agriculture, e.g. cattle, pig, sheep, goat, horse or donkey; or a plant, e.g. soybean, corn, sugarcane, rape, potato, cotton, rice, coffee, citrus, almond, tea.

In some embodiments, the medicament may be a medicament for parenterally administering to an animal, e.g. a medicament in the form of a tablet, a capsule, a drink, a drench, a granule, a paste, a bolus, a suppository.

In some embodiments, the medicament may be a medicament for parenterally administering to an animal, e.g., a medicament in the form for administering by means of injection (including intramuscular, subcutaneous, intravenous, intraperitoneal, etc.), implantation, showering or dipping.

In some embodiments, the medicament may be a medicament in the form for administering to a plant by means of spraying, pouring, dripping, washing or dusting.

The compounds of the present invention may be used for pest control on various plants including soybeans (e.g. 10-70 g/ha in some cases), corn (e.g. 10-70 g/ha in some cases), sugarcanes (e.g. 20-200 g/ha in some cases), alfalfa (e.g. 10-70 g/ha in some cases), brassica (e.g. 10-50 g/ha in some cases), rapes (e.g. Canola)(e.g. 20-70 g/ha in some cases), potatoes (including sweet potatoes) (e.g. 10-70 g/ha in some cases), cotton (e.g. 10-70 g/ha in some cases), rice (e.g. 10-70 g/ha in some cases), coffee (e.g. 30-150 g/ha in some cases), citrus (e.g. 60-200 g/ha in some cases), almonds (e.g. 40-180 g/ha in some cases), fruit vegetables (e.g. tomatoes, peppers, bell peppers, eggplants, cucumbers, pumpkins, etc.) (e.g. 10-80 g/ha in some cases), tea (e.g. 20-150 g/ha in some cases), bulbous vegetables (e.g. onions, leeks, etc.) (e.g. 30-90 g/ha in some cases), grapes (e.g., 30-180 g/ha in some cases), pomes (e.g., apples, pears, etc.) (e.g., 30-180 g/ha in some cases), and drupes (e.g., pears, plums, etc.) (e.g., 30-180 g/ha in some cases).

These pesticidal compositions may be used in the field of animal health, for example they are useful against parasitic invertebrate pests, more preferably against parasitic invertebrate pests inside animals or on animals' body surfaces. The animal may be a non-human animal, such as an animal associated with agriculture, e.g. cattle, pig, sheep, goat, horse or donkey.

Embodiments of the present disclosure are described in detail below. The embodiments described below are illustrative and are only used for explaining the present disclosure, but should not be construed as limitations to the present disclosure.

If no specific techniques or conditions are specified in the examples, the techniques or conditions described in literatures in the art or the product instructions shall be followed. The reagents and instruments used without indicating the manufacturer are all conventional products that can be purchased commercially.

In the explanation of the present description, the representation with reference to the terms "one embodiment", "some embodiments", "example", "specific example", or "some examples" etc. refers to the particular features, structures, materials or characteristics described in conjunction with the embodiment or example are included in at least one embodiment or example of the present disclosure. In the present description, the illustrative expressions of the above terms do not necessarily refer to the same embodiment or example. Furthermore, the particular features, structures, materials or characteristics described may be combined in any suitable manner in any one or more embodiments or examples. Besides, those skilled in the art may combine and associate different embodiments or examples and features of different embodiments or examples described in this description in cases without mutual contradiction.

Example 1: Acquisition of *Saccharopolyspora spinosa* with High Spinosad Production 1. Acquisition of Spinosad-Producing Strains (1) Strain Isolation In this example, a dilution method was used to isolate *Saccharopolyspora spinosa* from soil.

10 g of soil collected from different areas of Shandong Province was weighed and placed in a 250 ml Erlenmeyer flask filled with sterile water. The soil was fully shaken for 10 min to prepare a 0.1 g/mL soil suspension, and 10 glass beads were added to the soil suspension. Then, the solution was serially diluted in a 10-fold decrease and 10 separation culture media were coated with each concentration of solution. Among the colonies that eventually grew, *Streptomyces* samples with spore-producing colony morphology were selected for seed preservation. A total of 382 strains of bacteria were collected and isolated strains were obtained.

Wherein, the basic formula of the separation medium is: 3 g yeast extract, 10 g enzymatic casein (N-Z amine type A), and 5 g glucose was added into 1 L of distilled water, mixed, and dissolved thoroughly, and then the pH was adjusted to 7.0 with NaOH; the mixture was divided into 200 mL per bottle and 4 g agar was added into each bottle before sterilized at 115° C. for 30 min. After sterilization, the culture medium was cooled to about 65° C., nystatin was added to a final concentration of 50 μg/mL and nalidixic acid was added to a final concentration of 25 μg/mL to inhibit the growth of fungi and gram-negative bacteria, respectively.

(2) Acquisition of Spinosad Producing Strain 10 strains of the 382 strains are mixed and fermented, and the fermentation method is as follows:

(A) Fermentation Culturing

For each isolated strain, a single colony was picked and streaked onto another new isolation culture medium plate for growth. When it grew to a suitable state, a bacterial block of about 1 cm×1 cm was streaked onto the seed culture medium. Ten isolated strains were inoculated into a culture flask. The primary seeds were cultured at 250 rpm, 28° C., and 60% humidity for 96 hours. The primary seeds were observed under a microscope to see if they were contaminated by bacteria, as well as the growth status of the seeds. If they were not contaminated and had a good growth status, they were transferred to secondary seeds at a transfer rate of 1%. The culture conditions for the secondary seeds were the same as those for the primary seeds. After 60 hours of culture, the secondary seeds were examined under a microscope to see if they were contaminated by bacteria. If they were normal, fermentation transfer was performed at a transfer rate of 5%, and three parallel cultures were made for each flask of bacteria. The secondary seeds were transferred for fermentation at a transfer rate of 5%, and three parallels were set for each flask of seeds; the fermentation culture condition is: 250 rpm, 28° C., and 60% humidity for 12 days. Among them, the culture medium used for the primary seed and the secondary seed is seed culture medium.

Wherein, the seed culture medium and the fermentation culture medium have the following formula:

(a) Seed culture medium: 1 g glucose, 1 g yeast extract, 0.2 g N-Z amine type A, 2 g corn starch, 0.1 g ammonium sulfate, 2.5 g cottonseed cake powder and 0.2 g magnesium sulfate heptahydrate was added into every 100 mL distilled water, mixed and fully dissolved, and pH was adjusted to 7.0 with NaOH; seed culture medium was divided into 25 mL per bottle for seed culturing; sterilization was carried out at 121° C. for 30 min.

(b) Fermentation medium: 8 g glucose, 0.5 g yeast powder, 1 g protein powder, 2 g cottonseed cake powder, 0.2 g ammonium sulfate, 0.2 g dipotassium hydrogen phosphate, 0.4 g trisodium citrate, 0.3 g calcium carbonate and 5 g rapeseed oil was added into every 100 mL distilled water; mixed and fully dissolved, and pH was adjusted to 7.0 with NaOH; sterilization is carried out at 121° C. for 30 min; fermentation culture medium was divided into 25 mL per bottle for fermentation culturing; Note: Calcium carbonate is dispensed into each bottle.

(B) Screening of Spinosad Producing Strains 1 mL of fermentation broth was taken, and 2 mL of anhydrous ethanol was added into it. After ultrasonically bathing for 30 min, centrifugation was performed at 3500 rpm for 10 min. Supernatant was taken and filtered with 0.22 μm pore size filter membrane, and filtrate was collected. The filtrate was passed through a C18 reverse-phase high performance liquid chromatography (HPLC) column (5 μm, 250×4.6 mm Agilent, USA) at a flow rate of 1 ml/min, and a solvent system of acetonitrile:methanol:0.05% ammonium acetate buffer=4.5:4.5:1 was used as the eluent. The elution was performed at 25° C. A UV detector was used for UV absorption detection at a wavelength of 250 nm, and the eluate was collected. HPLC (Thermo Fisher) was used to determine the yield of spinosad in *Saccharopolyspora spinosa*, and compared it with standard samples (containing spinosad A and spinosad D components) to analyze whether the fermentation products contained spinosad. Spinosad was found to be produced in the 3rd and 21st flasks. The 20 strains in these two flasks were fermented one by one according to the fermentation method in (3) above. Finally, 3 strains that can produce spinosad were found, with yields of 33.8 mg/L, 121.5 mg/L, and 161.2 mg/L, respectively. They were named LK-001, LK-002, and LK-003, respectively.

2. Obtaining Strains with High Yield of Spinosad

The slant of LK-003 strain was prepared into spore suspension with physiological saline, filtered with absorbent cotton and adjusted to spore concentration of $10^5$-$10^6$/mL. 10 mL of single spore suspension was put into sterile 9 cm-diameter plate before the first round of mutagenesis was carried out by irradiating for 30 s at a distance of 20 cm from 15 W ultraviolet lamp, and then diluted and plated in a step-by-step manner in a 10-fold decrease.

Every 20 bacterial strains were divided into a group, fermented and cultured according to the abovementioned culture method (A), and strains were screened by the abovementioned screening method (B). A total of about 3,000 bacterial strains were screened, and the group with the highest yield, a total of 20 strains, was selected as the preliminary screened strains and named W100. The 20 strains were mixed for the second round of mutagenesis. The second round of mutagenesis adopted the chemical mutagenesis method, that is, the spore concentration was adjusted to $10^5$-$10^6$/mL, 1 mL was taken into a new centrifuge tube, and N-methyl-N'-nitro-N-nitrosoguanidine (MNNG) solution was added to make the mutagenic concentration 1 mg/mL MNNG. After incubation for half an hour, the spores were washed repeatedly with sterile water for three times and then graded dilutions were plated. About 3000 strains were screened using this method, and every 20 strains were divided into a group for mixed fermentation. The group with the highest yield, a total of 20 strains, was selected as the second screened strain and named W200. After 6 rounds of repeated mutagenesis (3 rounds of UV mutagenesis, 3 rounds of chemical mutagenesis, and the UV mutagenesis and chemical mutagenesis were performed alternately), the top group with 20 strains were selected as strains to be screened and named W600.

The 20 strains to be screened named W600 obtained in the last round were fermented one by one. According to the above detection method, spinosad A and spinosad D could be detected in the fermentation broth (FIG. 1), and spinosad A-iso, spinosad B, spinosad E, spinosad H, spinosad J, spinosad K, spinosad L, spinosad L2, spinosad L3, spinosad P and spinosad P-$CH_2$ could also be detected (FIG. 2). The strain with the highest yield was the 18th strain (FIG. 3), named W618, and the total shake flask yield of spinosad A and spinosad D was about 6 g/L.

3. Identification of Strain W618

(1) 16s rDNA Identification 16s rRNA gene sequence of strain W618 was amplified by PCR and sequenced to obtain the nucleotide sequence of 16S rRNA gene, and the specific sequence was shown in SEQ ID NO:1. Blast alignment showed that 16S rRNA gene of W618 had the highest sequence similarity with GENBANKACCESSION CP061007.1 (99.93%). Based on the above results, strain W618 was identified as *Saccharopolyspora spinosa.*

(2) Morphology of Bacteria

*Saccharopolyspora spinosa* is an aerobic Gram-positive actinomycete that can grow well on most culture media (such as YMS, calcium malate, etc.) and form aerial mycelium and white spores. The suitable growth temperature for the mycelium is 25° C.~35° C.

The morphology of strain W618 is shown in FIG. 4.

Based on the above identification results, the strain of the invention is *Saccharopolyspora spinosa.*

The strain W618 has been deposited in China Center for Type Culture Collection (CCTCC, address: Wuhan University, Wuhan, China) on Oct. 12, 2021, with the deposit accession number of CCTCC NO: M 20211261 and the taxonomic name of *Saccharopolyspora spinosa.*

Example 2: Comparison of Spinosad Production Abilities Between High-Yielding *Saccharopolyspora spinosa* Strains and Wild-Type *Saccharopolyspora spinosa* Strains 1. Fermentation Culturing of Wild-Type *Saccharopolyspora spinosa* Strains A wild-type strain NRRL18395 (Agricultural Research Service Culture Collection, USA) of *Saccharopolyspora spinosa* was obtained, and the wild-type *Saccharopolyspora spinosa* was fermented and cultured according to the fermentation method in Example 1.

2. Detection of the Ability of Wild Type *Saccharopolyspora spinosa* NRRL18395 for Producing Spinosad With reference to the above detection method, the fermentation product was analyzed to see whether it contained spinosad, and the production of spinosad in the fermentation product was detected to be 83.5 mg/L.

3. Comparison of the Abilities for Producing Spinosad Between *Saccharopolyspora spinosa* W618 and Wild-Type *Saccharopolyspora spinosa* NRRL18395

As described in Example 1, the yield of spinosad produced by fermentation with *Saccharopolyspora spinosa* W618 provided by the present disclosure is as high as about 6 g/L. The yield of wild-type *Saccharopolyspora spinosa* is 83.5 mg/L, and the above results indicate that the ability for producing spinosad of W618 obtained by screening in the present disclosure is significantly higher than that of wild-type *Saccharopolyspora spinosa*. Therefore, *Saccharopoly-* spora spinosa W618 can be developed as an industrial strain with high spinosad production.

Although examples of the present disclosure have been shown and described above, it is to be understood that the above examples are illustrative and are not to be construed as limitations of the present disclosure. A person skilled in the art may change, modify, replace and vary the above examples within the scope of the present disclosure.

culture medium, and a pH of the seed culture medium and/or the fermentation medium is adjusted with a pH adjusting agent.

8. The method according to claim 5, wherein the fermentation is cultured at 200-300 rpm with a temperature of 10-40° C. and a humidity of 50-70%.

9. A method for killing insects, animals of subclass Acari, or nematodes, comprising administering a medicament com-

What is claimed is:

1. A *Saccharopolyspora spinosa* strain W618 deposited at China Center for Type Culture Collection under accession number CCTCC NO: M 20211261.

2. A pesticidal composition comprising the strain according to claim 1.

3. The pesticidal composition according to claim 2, further comprising one or more compounds selected from the group consisting of: organophosphorus compounds, carbamate compounds, synthetic pyrethroid compounds, acyl urea compounds, insect growth regulators, insect hormone analogs, neonicotinoids, nicotinoid compounds, macrolide compounds, insecticidal, acaricidal, molluscicidal, and nematicidal compounds or active ingredients, and phagocytic stimulants.

4. The pesticidal composition according to claim 2, further comprising a pharmaceutically acceptable carrier.

5. A method for preparing the pesticidal composition of claim 2, comprising seeding the strain into a culture medium for fermentation.

6. The method according to claim 5, wherein the culture medium comprises seed culture medium and fermentation culture medium.

7. The method according to claim 5, wherein the culture medium comprises seed culture medium and fermentation prising the pesticidal composition according to claim 2 to an animal or a plant associated with agriculture.

10. The pesticidal composition according to claim 3, wherein the organophosphorus compounds are selected from one or more of the following compounds: acephate, azinphos-methyl, cadusafos, trichloronate, chlorpyrifos, coumaphos, dematon, demeton, diazinon, dichlorvos, dimethoate, EPN, erthoate, ethoprophos, etrimfos, fenamiphos, fenitrothion, fensulfothion, fenthion, fonofos, formothion, fosthiazate, heptenophos, malathion, methamidophos, methyl parathion,mevinphos, monocrotophos, parathion, phorate, phosalone, phosmet, phosphamidon, phosphocarb, phoxim, profenofos, propaphos, propetamphos, prothiofos, pirimiphos-methyl, pirimiphos-ethyl, quinalphos, sulprofos, tebupirimphos, temephos, terbufos, tetrachlorvinphos, thiafenox, thiometon, triazophos and trichlorfon;

the carbamate compounds are selected from one or more of the following compounds: aldicarb, bendiocarb, benfuracarb, bensultap, BPMC, butoxycarbocim, carbaryl, furadan, carbosulfan, cloethocarb, ethiofencarb, fenobucarb, furathiocarb, methiocarb, isoprocarb, methomyl, methomyl, pirimicarb, promecarb, propoxur, thiodicarb and thiofurox;

the synthetic pyrethroid compounds are selected from one or more of the following compounds: acrinathrin, allethrin, β-cyfluthrin, bifenthrin, bioresmethrin, cyfluthrin, cyhalothrin, λ-cyhalothrin, γ-cyhalothrin, cypermethrin, α-cypennethrin, ζ-cypermethrin, deltamethrin, esfenvalerate, fenvalerate, fenfluthrin, fenpropathrin, flucythrinate, flumethrin, fluvalinate, τ-fluvalinate, fubfenprox, permethrin, protrifenbute, resmethrin, silafluofen, tefluthrin, tetramethrin, tralomethrin, etofenprox, natural pyrethroids, tetramethrin, S-allethrin, fenfluthrin and prallethrin;

the acyl urea compounds, insect growth regulators and insect hormone analogs are selected from one or more of the following compounds: buprofezin, chromfenozide, chlorfluazuron, diflubenzuron, fenoxycarb, flufenoxuron, halofenozide, hexaflumuron, hydroprene, lufenuron, methoprene, methoxyfenozide, novaluron, pyriproxyfen, teflubenzuron and benzamide, N-[3,5-dichloro-2-fluoro-4-(1,1,2,3,3,3-hexafluoropropoxy)phenyl]-N'-(2,6-difluorobenzoyl)urea;

the neonicotinoids and nicotinoid compounds are selected from one or more of the following compounds: acetamiprid, AKD-1022, cartap, TI-435, clothianidin, MTI-446, dinotefuran, imidacloprid, nicotine, nitenpyram, thiamethoxarn, thiacloprid;

the macrolide compounds are selected from one or more of the following compounds: avermectin, milbemycin, abamectin, ivermectin, milbemycin and emamectin benzoate;

the insecticidal, acaricidal, molluscicidal and nematicidal compounds or active ingredients are selected from one or more of the following compounds: allethrin, amitraz, azdirachtin, azocyclotin, bifenazate, bromopropylate, chlordimeform, chlorfenapyr, chlofentezine, chlorobenzilate, chlordane, cyhexatin, cyromazine, DDT, dicofol, dieldrin, DNOC, endosulfan, ethoxazole, fenazaquin, cyhexatin, fenpyroximate, p-fenpyroximate, fipronil, fluoropheniminothiazole hexythiazox, IKI-220, indoxacarb, lindane, methiocarb, metaldehyde, methoxychlor, neem, petroleum and vegetable oils, pyridaben, pymetrozine, pyrimidifen, rotenone, S-1812, S-9539, spirodiclofen, sulphur, tebufenpyrad, tetradifon, menazon, insecticidal plant extracts, preparations containing insecticidal nematodes, piperonyl butoxide, sesam ex, safroxan and dodecyl imidazole; and/or the phagocytic stimulants are selected from cucurbitacin and/or sugar.

11. The pesticidal composition according to claim 4, wherein the carrier is a liquid carrier or a solid carrier.

12. The pesticidal composition according to claim 11, wherein the liquid carrier is selected from one or more of: aliphatic ketones, complex alcohols, or aromatic compounds; and/or the solid carrier is selected from one or more of attapulgite clay, montmorillonite clay, diatomaceous earth or purified silicate.

13. The pesticidal composition according to claim 2, wherein the pesticidal composition is in a dosage form selected from wettable powders, soluble powders, emulsifiable concentrates, aqueous suspensions, dispersible oil suspensions, aqueous emulsions, aerosols, microemulsions and water-dispersible granules.

14. The method according to claim 5, wherein the pesticidal composition is selected from one or more of spinosad A, spinosad A iso, spinosad B, spinosad C, spinosad D, spinosad E, spinosad F, spinosad G, spinosad H, spinosad J, spinosad K, spinosad L, spinosad L2, spinosad L3, spinosad P, and spinosad P-CH$_2$.

15. The method according to claim 5, wherein the pesticidal composition comprises spinosad A and spinosad D.

16. The method according to claim 6, wherein the seed culture medium comprises: 0.8-1.2 parts by mass of glucose, 0.8-1.2 parts by mass of yeast extract, 0.16-0.24 parts by mass of N-Z amine type A, 1.8-2.4 parts by mass of corn starch, 0.08-0.12 parts by mass of ammonium sulfate, 2-3 parts by mass of cottonseed meal, 0.16-0.24 parts by mass of magnesium sulfate heptahydrate, and 80-120 parts by mass of water, wherein the water is distilled.

17. The method according to claim 6, wherein the seed culture medium is composed of: 1 part by mass of glucose, 1 part by mass of yeast extract, 0.2 parts by mass of N-Z amine type A, 2 parts by mass of corn starch, 0.1 parts by mass of ammonium sulfate, 2.5 parts by mass of cottonseed meal, 0.2 parts by mass of magnesium sulfate heptahydrate, and 100 parts by mass of water, wherein the water is distilled.

18. The method according to claim 6, wherein the fermentation medium comprises: 6.4-9.6 parts by mass of glucose, 0.4-0.6 parts by mass of yeast powder, 0.8-1.2 parts by mass of protein powder, 1.6-2.4 parts by mass of cottonseed meal, 0.32-0.48 parts by mass of trisodium citrate, 0.16-0.24 parts by mass of dipotassium hydrogen phosphate, 0.24-0.36 parts by mass of calcium carbonate, 0.16-0.24 parts by mass of ammonium sulfate, 4-6 parts by mass of rapeseed oil, and 80-120 parts by mass of water, wherein the water is distilled.

19. The method according to claim 6, wherein the fermentation medium is composed of: 8 parts by mass of glucose, 0.5 parts by mass of yeast powder, 1 part by mass of protein powder, 2 parts by mass of cottonseed meal, 0.4 parts by mass of trisodium citrate, 0.2 parts by mass of dipotassium hydrogen phosphate, 0.3 parts by mass of calcium carbonate, 0.2 parts by mass of ammonium sulfate, 5 parts by mass of rapeseed oil, and 100 parts by mass of water, wherein the water is distilled.

20. The method according to claim 5, wherein a pH value of the culture medium is 6.8-7.2.

21. The method according to claim 5, wherein a pH value of the culture medium is 7.0.

22. The method according to claim 7, wherein the pH adjuster is a base.

23. The method according to claim 22, wherein the base is selected from one or more of sodium hydroxide, potassium hydroxide, sodium carbonate, or sodium bicarbonate.

24. The method according to claim 5, wherein the fermentation is cultured at 250 rpm with a temperature of 28° C. and a humidity of 60%.

25. The method according to claim 9, wherein the animal is selected from cattle, pig, sheep, goat, horse or donkey; and/or the plant is selected from soybean, corn, sugarcane, rape, potato, cotton, rice, coffee, citrus, almond, or tea.

26. The method according to claim 9, wherein:

the medicament is enterally administered to an animal in the form of a tablet, a capsule, a drink, a drench, a granule, a paste, a bolus, a suppository;

the medicament is parenterally administered to an animal via intramuscular subcutaneous, intravenous, or intraperitoneal injection, by implantation, showering, dipping, spraying, pouring, dripping, washing or dusting; and/or the medicament is administered to a plant by spraying, pouring, dripping, washing or dusting.

27. The pesticidal composition according to claim 12, wherein the liquid carrier is selected from one or more of: cyclohexanone, 2-ethoxyethanol, xylene, naphthalene, and olefinic parts of petroleum.

\* \* \* \* \*